United States Patent [19]

Stolowitz et al.

[11] Patent Number: 4,863,870

[45] Date of Patent: Sep. 5, 1989

[54] METHOD OF THIOACYLATION PEPTIDE SEQUENCING WITH ALCOHOLYSIS OF THIAZOLINONES

[75] Inventors: Mark L. Stolowitz, Long Beach; Beth A. Paape, San Pedro; Anne E. DeVaux, Marina Del Rey, all of Calif.

[73] Assignee: Bio-Affinity Systems, Inc., Torrance, Calif.

[21] Appl. No.: 166,551

[22] Filed: Mar. 10, 1988

[51] Int. Cl.[4] ...................... G01N 21/25; G01N 33/68
[52] U.S. Cl. ........................................ 436/89; 436/92
[58] Field of Search .................... 436/89, 92, 161, 164

[56] References Cited

U.S. PATENT DOCUMENTS

| | | | |
|---|---|---|---|
| 3,975,155 | 8/1976 | Geyer | 436/92 X |
| 4,110,378 | 8/1978 | Geyer | 436/92 X |
| 4,548,904 | 10/1985 | Kent et al. | 436/89 |
| 4,652,530 | 3/1987 | Rothman | 436/92 |

OTHER PUBLICATIONS

Previero et al, Chemical Abstracts, vol. 84, No. 21, Abstract No. 147268m, 5/24/76.
Tsugita et al. Chemical Abstracts, vol. 106, No. 11, Abstract No. 81238r, 3/16/87.

*Primary Examiner*—Robert J. Hill, Jr.
*Attorney, Agent, or Firm*—Blakely, Sokoloff Taylor, Zafman

[57] ABSTRACT

A sequencing method which exploits the thioacylation degradation of polypeptides and proteins is disclosed. The process involves reaction of the N-terminal amino acid of a polypeptide with an excess of a thioacylating reagent. After sufficient time to insure quantitative coupling and removal of excess reagent, the N-thioacyl polypeptide is subjected to cleavage by acid which affords a 2-substituted-5(4H)-thiazolinone of the N-terminal amino acid. Subsequent addition of a large excess of an aliphatic primary or secondary alcohol, either directly to the cleavage acid or after its removal, yields the corresponding N-thioacyl amino acid ester, a stable compound suitable for chromatographic separation and subsequent detection by contemporary methods of high pressure liquid chromatography.

13 Claims, No Drawings

METHOD OF THIOACYLATION PEPTIDE SEQUENCING WITH ALCOHOLYSIS OF THIAZOLINONES

FIELD OF THE INVENTION

The invention relates to sequencing a polypeptide or protein molecule in order to determine its amino acid sequence, and more particularly, to the thioacylation degradation method.

BACKGROUND OF THE INVENTION

Proteins and polypeptides are naturally occuring, and recently, synthetically prepared compounds that are compound of long chains of amino acids. Proteins are found throughout living things and function as enzymes, hormones, immunoglobulins, structural elements, and other constituents of living things. Research regarding the structure and function of a protein often requires that the amino acid sequence (primary structure) of the protein be determined in order for a protein or the polypeptide constituents thereof to be synthesized, the sequence of amino acids must be determined. In the search involving the function of proteins, the primary structure must first be determined in an attempt to elucidate the mechanism of action of the protein. In recombinant DNA methodology, the primary structure must be determined to elucidate the corresponding structure of a DNA or RNA encoding the same.

The sequence of amino acids in proteins or polypeptides is commonly determined by stepwise chemical degradation in which single amino acids are derivatized and removed one by one from the end of the polypeptide to be identified. The standard method, the Edman degradation (Edman, P., *Acta Chem. Scand.*, (1950) 4, 283), is the preferred method. Alternatively, thioacylation has attracted considerable attention as an effective alternative to the Edman degradation, owing to the particularly mild conditions under which it is employed.

The thioacylation degradation of proteins and polypeptides was first proposed by Barrett (Barrett, G. C., *Chem. Comm.*, (1967) 487) as an alternative to the Edman degradation. The process involves reacting the N-terminal amino acid of a starting polypeptide immobilized on an insoluble support (heterogeneous phase reaction) with a thioacylating reagent in an alkaline aqueous or anhydrous solvent. The excess reagent is removed by washing of the immobilized polypeptide, and byproducts of the reaction resulting from the decomposition of the reagent are similarly removed, to yield the N-thioacyl polypeptide, Formula I, wherein X is an alkyl or aryl substituent and R is representative of the various amino acid side chains. Thioacylating reagents exhibit low solubility in aqueous media which limits their use in homogenous phase techniques. This limitation was overcome by the advent of solid phase and pulsed liquid methods.

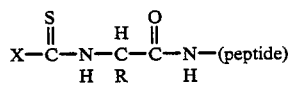

Formula I

Various activated carbodithioic esters, thiono esters and thiono imides including carboxymethyl dithiobenzoate, cyanomethyl dithiobenzoate, m-nitrobenzoylthionocholine, N-thiobenzoylsuccinimide, thioacetylthioglycholic acid and methyl dithoacetate have been employed as reagents for the sequential degradation of polypeptides. Aminolysis of carbodithioic esters is susceptible to general base catalysis and experimental conditions under which simple alkyl esters of aliphatic dithioacids, such as methyl dithioacetate, behave as satisfactory thiocylating reagents have been reported (Previero, A., Gourdol, A., Derancourt, J. and Coletti-Previero, M.-A., *FEBS Lett.*, (1975) 51, 68).

In the second step, the N-thiocayl polypeptide is subjected to cleavage by volatile anhydrous acid to afford the 2-substituted-5(4H)-thiazolinone of the N-terminal amino acid, Formula II, wherein X is an alkyl or aryl substituent and R is representative of the various amino acid side chains. Thioacylation offers a significant advantage over the Edman degradation in that the cleavage reaction is short in duration and occurs under relatively mild conditions. Also liberated during the cleavage reaction is the salt of the residual polypeptide, which is the starting polypeptide with the N-terminal amino acid removed.

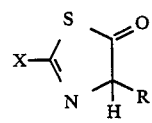

Formula II

2-Methyl-5(4H)-thiazolinones were historically identified by hydrolytic regeneration of the free amino acids (Mross, Jr., G. A., (1971) *Ph.D. Dissertation, University of California, San Diego*). Consequently, serine, threonine and tryptophan were not recovered in high yield owing to their instability during hydrolysis. Alternatively, 2-methyl-5(4H)-thiazolinones have been identified by gas liquid chromatography, preferably, after reaction with excess acetic anhydride in pyridine or acetyl chloride in TFA (Simpson, D. L., Hranisewljevic, J. and Davidson, E. A., *Biochemistry*, (1972) 11, 1849) which yields the corresponding 5-O-acetyl-2-metylthiazoles. 2-Phenyl-5(4H)-thiazolinones have been identified directly by mass spectrometry and by thin layer chromatography after conversion to the corresponding N-thiobenzoyl amino acid anilides (Barrett, G. C. and Khokhar, A. R., *J. Chromatog.*, (1969) 39, 47).

In the Edman degradation, the product of the cleavage reaction is the 2-anilino-5(4H)-thiazolinone (ATZ). This unstable species is then converted to its isomer, the 3-phenyl-2-thiohydantoin (PTH), Formula III, wherein R is representative of the various amino acid side chains.

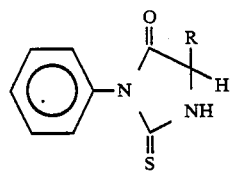

Formula III

Conventional techniques for conversion involve heating the ATZ (50°–80° C.) under nitrogen in hydrochloric acid, anhydrous methanolic hydrochloric acid or anhydrous methanolic trifluoroacetic acid. Conversion with aqueous acid invariably results in deamidation of asparagine and glutamine to their respective acids, while anhydrous methanolic hydrochloric and trifluoroacetic acids cause esterification of acidic residues.

Certain PTH amino acids require adjustment of pH or time for quantitative conversion while other PTH amino acids tend to decompose during the conversion reaction. While alcoholysis of ATZ amino acids has been recognized as an intermediate reaction during conversion in alcoholic acid, the isolation of the intermediate phenylthiocarbamyl amino acid esters is not feasible as a consequence of their tendency toward conversion to the corresponding PTH amino acids (Tarr, G. E., in Methods of Protein Microcharacterization, Shively, J. E., Ed., Humana Press, Clifton, N.J. (1986) 175–179).

SUMMARY OF THE INVENTION

A novel sequencing method which exploits the thioacylation degradation of polypeptides and proteins is disclosed. The process involves reaction of the N-terminal amino acid of a polypeptide with an excess of a thioacylating reagent. After sufficient time to insure quantitative coupling and removal of excess reagent, the N-thioacyl polypeptide is subjected to cleavage by acid which affords a 2-substituted-5(4H)-thiazolinone of the N-terminal amino acid. Subsequent addition of a large excess of an aliphatic primary or secondary alcohol, either directly to the cleavage acid or after its removal, yields the corresponding N-thioacyl amino acid ester, a stable compound suitable for chromatographic separation and subsequent detection by contemporary methods of high pressure liquid chromatography.

It is an object of this invention to provide a peptide sequencing system which affords stable derivatives suitable for use with contemporary methods of liquid chromatographic separation and detection.

It is another object of this invention to provide a peptide sequencing system which utilizes mild cleavage conditions as compared to the Edman degradation.

It is yet another object of this invention to provide a peptide sequencing system which affords a stable derivative immediately after cleavage of the N-terminal amino acid and requires no subsequent conversion reaction.

DETAILED DISCUSSION

The present invention relates to a novel method which exploits the thioacylation degradation of polypeptides to determine the primary structure of a polypeptide or protein. The process first involves reaction of the N-terminal amino acid of a starting polypeptide preferably but not necessarily immobilized on an insoluble support (heterogeneous phase reaction) with an excess of a thioacylating reagent of the form X-C(S)W, where X is as defined below and W is a leaving group, such as —SR', —OR', or —NR'R" with R' and R" being alkyl, aryl, acyl, or substituted derivatives thereof. Preferred thioacylating reagents include carboxymethyl dithiobenzoic acid, cyanomethyl dithiobenzoate and carboxymethyl dithiophenylacetic acid. The reaction occurs in the presence of an acid scavenger in alkaline aqueous or anhydrous solvent, at room temperature or at elevated temperature. After sufficient time to ensure thioacylation of the polypeptide, a few minutes to several hours and generally 15 to 45 minutes, the excess reagent is removed by washing of an immobilized polypeptide, and byproducts of the reaction resulting from the decomposition of the reagent are similarly removed, to yield a N-thioacyl polypeptide of general formula IV wherein X is an aryl or aryl-alkyl substituent which contains a moiety detectable during chromatographic separation, and is preferably phenyl, m-nitrophenyl, benzyl or p-nitrobenzyl, R represents the various amino acid side chains and -(peptide) represents the remainder of the starting peptide, not including the N-terminal amino acid.

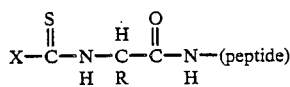

Formula IV

The compound of general formula IV is next subjected to cleavage by reaction with a volatile anhydrous perfluorinated carboxylic acid, preferably trifluoroacetic acid (TFA), at room temperature or at elevated temperature, to yield the 2-substituted-5(4H)-thiazolinone of general formula V and the salt of the residual polypeptide, which is the starting polypeptide with the N-terminal amino acid removed.

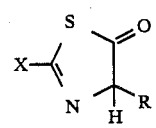

Formula V

After separation from the salt of the residual polypeptide and preferably after removal of excess acid in vacuo or by evaporation under a stream of nitrogen gas at elevated temperature, the compound of general formula V is next reacted with a large excess of an aliphatic primary or secondary alcohol, neat, at room temperature or at elevated temperature, to yield the corresponding N-thioacyl amino acid ester of general formula VI, wherein X is an aryl or aryl-alkyl substituent, R represents the various amino acid side chains and R' is an alkyl substituent. Preferred alcohols are methanol, ethanol, 2-propanol, and n-propanol, especially methanol. If the alcoholysis reaction is conducted in the presence of the cleavage acid, some esterification of the aspartic acid and glutamic acid side chains is to be expected. The process described above is then repeated for each N-terminal amino acid in the polypeptide, until the entire polypeptide is sequenced.

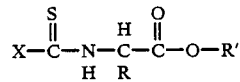

Formula VI

The N-thioacyl amino acid esters are stable compounds not subject to subsequent conversion as are the corresponding phenylthiocarbamoyl amino acid esters. This is advantageous in that the various deleterious side reactions associated with the conversion of 2-anilino-5(4H)-thiazolinones are avoided.

The N-thioacyl amino acid esters which result from the aforedescribed process are ordinarily subjected to chromatographic analysis, most commonly reverse phase high pressure liquid chromatography (HPLC). The compounds may be detected by ultraviolet absorbance or other means. Standard methods, equipment, solvents, buffers, reaction sequences of manual and automatic sequencing can be used with minor modifications where necessary to accomodate the alcoholysis of the 2-substituted-5(4H)-thiazolinone. Preferred automated methods of sequencing include the spinning cup, solid phase, pulsed liquid and gas phase methods. Adjustment of chromatographic mobile phase constituents may be necessary to optimize resolution and sensitivity. The following examples describe the preparation of chromatographic standards and the use of the process in the sequencing of peptides.

EXAMPLE I

Preparation of Carboxymethyl Dithiophenylacetate

Methyl Dithiophenylacetate

A mixture of phenylacetic acid (60 grams, 0.44 mole) and 2,4-bismethylthio-1,3,2,4-dithiaphosphetane 2,4-disulfide (85 grams, 0.30 mole) in toluene (125 mL) was stirred under reflux for 3 hours. The reaction mixture was allowed to cool to room temperature then diluted with hexanes (750 mL). The resulting solution was decanted from the settled solid mass and the solvent was removed in vacuo. The viscous liquid thus obtained was purified by flash chromatography on silica gel utilizing hexanes as eluent. Methyl dithiophenylacetate is obtained in approximately 50% yield as an orange liquid.

Carboxymethyl Dithiophenylacetate

To a well stirred solution of methyl dithiophenylacetate (16.2 grams, 0.089 mole) in methanol (50 mL) was added anhydrous sodium hydrogen sulfide (5.6 grams, 0.10 mole). The mixture was stirred overnight at room temperature, and the solvent removed in vacuo. The solid salt thus obained was taken up in tetrahydrofuran (125 mL). To the solution was added bromoacetic acid (12.4 grams, 0.089 mole). The resulting mixture was stirred for 2 hours at room temperature, and the solvent removed in vacuo. The resulting solid was taken up in 5% (w/v) aqueous sodium bicarbonate, then washed twice with chloroform. The aqueous layer was acidified by the addition of concentration HCl and then extracted three times into diethyl ether. The combined ethereal extracts were dried over anhydrous $Na_2SO_4$. The solvent was then finally removed in vacuo to afford carboxymethyl dithiophenylacetate, an orange solid, in 94.5% yield.

EXAMPLE II

Preparation of N-Thiophenylacetyl Amino Acid Methyl Esters

Amino acid methyl esters (2 mmole) in methanol (10–15 mL) were reacted with methyl dithiophenylacetic acid (1 mmole) and triethylamine (TEA) (2 mmole) for up to 12 hours at room temperature with constant agitation, the change toward pale yellow in color indicating the progress of the reaction. The reaction was monitored by thin layer chromatography on silica gel plates. With chloroform as eluent, unreacted reagent ran at the solvent front while the N-thiophenylacetyl amino acid methyl esters were found on the lower half of the plate. The reaction products in methanol were purified by extraction with hexane and then concentrated by rotary evaporation. The concentrated products were dissolved in ethyl acetate and then washed with 10% (w/v) citric acid and water. The ethyl acetate solution was then dried over anhydrous $Na_2SO_4$. The solvent was removed by rotary evaporation to afford the various standards.

EXAMPLE III

Thioacylation Degradation

The peptide Fmoc-Ala-Phe-Gly-Ile-Ala-OH (3 mg) was immobilized on N-(2-aminoethyl)-3-aminopropyl glass (15 mg, 75 angstrom pore, 200–400 mesh) after activation with diisopropylcarbodiimide in N,N-dimethylformamide (DMF). The Fmoc group was subsequently removed by reaction with 20% (v/v) piperidine in DMF. Carboxymethyl dithiophenylacetic acid (DTPA) was synthesized as described above. The immobilized peptide was sequenced manually by thioacylation degradation as follows; the peptide was first washed with aliquots of methanol (3×3 ml.) followed by 10% (v/v) TEA in methanol (3×3 mL). To the reaction vessel was added 1 mL of 20% (v/v) TEA in methanol and 1 mL of 10% (w/v) DTPA in methanol. The vessel was agitated constantly for 30 min. while maintained at 45° C. Excess reagent was washed from the immobilized peptide with aliquots of methanol (3×5 mL), DMF (3×3 mL), dichloromethane (3×3 mL) and methanol (3×3 mL). The immobilized peptide was the dried under a stream of nitrogen. The thiazolinone was liberated by the addition of TFA (1.5 mL) to the immobilized peptide. After 30 minutes at room temperature, the TFA was collected and the immobilized peptide washed with methanol (2×1.5 mL). The methanol washes were collected and added to the TFA. The alcoholic TFA solution was then concentrated by evaporation under a stream of nitrogen at 50° C. The residues were taken up in acetonitrile and analyzed as described below. The process was repeated for each N-terminal amino acid in the peptide.

EXAMPLE IV

Analysis and Detection

The N-thiophenylacetyl amino acid esters were separated by gradient elution HPLC on an IBM Instruments 5u, 4.6 mm×150 mm, C18 column. The HPLC system was comprised of an IBM 9560 Ternary Gradient Liquid Chromatograph and an IBM 9505 Automatic Sample Handler. Sample volumes of 20 uL were utilized. The ultra violet detector was a Kratos 757 with a 12 uL flow cell. The ultraviolet absorbance was measured at 265 nm. The mobile phase (%A) was prepared by the addition of 10.0 mL of acetic acid, 4.0 mL of TEA and 2.0 mL of TFA to one liter of water. The final pH was adjusted to 3.1. The flow rate was 1.5 mL/min. Samples were injected in acetonitrile and gradient elution was accomplished by the adition of acetonitrile (%B) to the mobile phase according to the following table:

| Time | % A | % B |
| --- | --- | --- |
| 0 | 80 | 20 |
| 8.0 | 60 | 40 |
| 8.1 | 57 | 43 |
| 19.0 | 45 | 55 |
| 21.0 | 45 | 55 |
| 21.1 | 80 | 20 |

We claim:
1. A method for determining the identity of an N-terminal amino acid of a polypeptide comprising the steps of:
 (a) providing a starting polypeptide having an N-terminal amino acid;
 (b) reacting said polypeptide with a thioacylating reagent of the form X-C(S)W wherein X is aryl or aryl-alkyl and W is a leaving group, to form a compound having the formula IV, wherein R represents an amino acid side chain and -(peptide) represents the starting peptide, not including the N-terminal amino acid;

$$\underset{\underset{H}{|}\;\;\underset{R}{|}}{X-\overset{S}{\overset{\|}{C}}-N-\overset{H}{\underset{|}{C}}-\overset{O}{\overset{\|}{C}}-N-(\text{peptide})} \qquad \text{IV}$$

(c) cleaving the compound of formula IV with a volatile anhydrous acid to form a residual polypeptide, which comprises the starting polypeptide with the N-terminal amino acid removed, and a 2-substituted-5(4H)-thiazolinone compound of general formula V;

$$X-\underset{N\;\;\underset{H}{|}\;R}{\overset{S}{\diagup}\diagdown\overset{O}{\diagdown}} \qquad \text{V}$$

(d) reacting the compound of general formula V with an aliphatic primary or secondary alcohol to yield a corresponding N-thioacyl amino acid ester of general formula VI wherein R' is an alkyl substituent;

$$\underset{\underset{H}{|}\;\;\underset{R}{|}}{X-\overset{S}{\overset{\|}{C}}-N-\overset{H}{\underset{|}{C}}-\overset{O}{\overset{\|}{C}}-O-R'} \qquad \text{VI}$$

(e) identifying the N-thioacyl amino acid ester of general formula VI.

2. The method of claim 1 wherein said polypeptide is immobilized on a solid support prior to step b.

3. The method of claim 1, wherein said thioacylating reagent is selected from the group consisting of X-C(S)SR', X-C(S)OR' and X-C(S)NR'R" wherein R' and R" are alkyl, aryl, acyl or substituted derivatives thereof.

4. The method of claim 3 wherein said thioacylating reagent is selected from the group consisting of carboxymethyl dithiobenzoic acid, cyanomethyl dithiobenzoate and carboxymethyl dithiophenylacetic acid.

5. The method of claim 1 wherein step b occurs in the presence of excess thioacylating reagent.

6. The method of claim 5 further comprising removing excess thioacylating reagent prior to step c.

7. The method of claim 1 wherein step b occurs in the presence of an acid scavenger in an alkaline aqueous solvent or an anhydrous solvent.

8. The method of claim 1 wherein said volatile anhydrous acid is trifluoroacetic acid.

9. The method of claim 1 further comprising separating the compound of formula V from said residual polypeptide and separating said acid from said compound of formula V.

10. The method of claim 1 wherein said aliphatic primary or secondary alcohol is selected from the group consisting of methanol, ethanol, 2-propanol and n-propanol.

11. The method of claim 10 wherein said aliphatic primary or secondary alcohol is methanol.

12. The method of claim 1 wherein X is phenyl, m-nitrophenyl, benzyl or p-nitrobenzyl.

13. The method of claim 12 wherein X is phenyl.

* * * * *